United States Patent
Hassler, Jr. et al.

(10) Patent No.: US 7,374,565 B2
(45) Date of Patent: May 20, 2008

(54) BI-DIRECTIONAL INFUSER PUMP WITH VOLUME BRAKING FOR HYDRAULICALLY CONTROLLING AN ADJUSTABLE GASTRIC BAND

(75) Inventors: William L. Hassler, Jr., Carlsbad, CA (US); Daniel F. Dlugos, Jr., Middletown, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 301 days.

(21) Appl. No.: 10/857,763

(22) Filed: May 28, 2004

(65) Prior Publication Data

US 2005/0277960 A1    Dec. 15, 2005

(51) Int. Cl.
    *A61B 17/08*    (2006.01)
    *A61K 9/22*     (2006.01)
(52) U.S. Cl. .................................. 606/151; 604/891.1
(58) Field of Classification Search ................ 606/151, 606/153; 600/207; 417/472, 15, 394; 604/890.1, 604/891.1, 99.01, 288.01, 288.02, 288.03, 604/288.04; 607/61
    See application file for complete search history.

(56) References Cited

U.S. PATENT DOCUMENTS

| | | | |
|---|---|---|---|
| 4,060,178 A * | 11/1977 | Miller | 222/14 |
| 4,505,710 A * | 3/1985 | Collins | 604/891.1 |
| 4,525,165 A * | 6/1985 | Fischell | 604/131 |
| 4,581,018 A | 4/1986 | Jassawalla et al. | |
| 4,592,339 A | 6/1986 | Kuzmak et al. | |
| 5,100,100 A * | 3/1992 | Benson et al. | 251/129.06 |
| 5,226,429 A | 7/1993 | Kuzmak | |
| 5,449,368 A | 9/1995 | Kuzmak | |
| 5,507,737 A | 4/1996 | Palmskog | |
| 5,667,504 A * | 9/1997 | Baumann et al. | 604/891.1 |
| 5,715,837 A | 2/1998 | Chen | |
| 5,733,313 A | 3/1998 | Barreras, Sr. et al. | |

(Continued)

FOREIGN PATENT DOCUMENTS

WO    WO 00 72899    12/2000

(Continued)

OTHER PUBLICATIONS

EP Search Report for Application No. 05253316.3, dated Oct. 7, 2005.

*Primary Examiner*—Michael J. Hayes
*Assistant Examiner*—Lindsey Bachman
(74) *Attorney, Agent, or Firm*—Frost Brown Todd, LLC (57) ABSTRACT

An implantable artificial sphincter system provides long-term adjustment via transcutaneous energy transfer (TET), minimizing invasive adjustment through adding or removing fluid via a syringe. An infuser device provides bi-directional fluid transfer via a flexible conduit to a sphincter band, such as a gastric band, by a combination of thermo-dynamic actuation and a piezo-electrically disengaged drum brake assembly that thereby achieves a desirable small volume device. A propellant within a propellant cavity surrounds a metal bellows accumulator biased at body temperature to either expand or collapse the bellows accumulator with the opposite direction of movement effected by a thermal element that heats in combination with a negatively-biased propellant or cools in combination with a positively-biased propellant. A drum brake assembly locks the metal bellows accumulator in place between adjustments by thermodynamic actuation by activating piezo-electric stack actuators that disengage calipers from a brake drum attached to the bellows accumulator.

15 Claims, 7 Drawing Sheets

U.S. PATENT DOCUMENTS

| | | |
|---|---|---|
| 5,974,873 A | 11/1999 | Nelson |
| 6,058,330 A | 5/2000 | Borza |
| 6,102,678 A | 8/2000 | Peclat |
| 6,102,922 A | 8/2000 | Jakobsson et al. |
| 6,315,769 B1 | 11/2001 | Peer et al. |
| 6,327,504 B1 | 12/2001 | Dolgin et al. |
| 6,366,817 B1 | 4/2002 | Kung |
| 6,416,495 B1 | 7/2002 | Kriesel et al. |
| 6,430,444 B1 | 8/2002 | Borza |
| 6,461,992 B1 | 10/2002 | Sechrist et al. |
| 6,463,329 B1 | 10/2002 | Goedeke |
| 6,470,892 B1 | 10/2002 | Forsell |
| 6,475,136 B1 * | 11/2002 | Forsell ........................ 600/37 |
| 6,482,177 B1 | 11/2002 | Leinders |
| 6,542,350 B1 | 4/2003 | Rogers |
| 7,011,621 B2 * | 3/2006 | Sayet et al. ................... 600/30 |
| 7,191,007 B2 | 3/2007 | Desai et al. |
| 2003/0105385 A1 | 6/2003 | Forsell |
| 2003/0114729 A1 | 6/2003 | Forsell |
| 2005/0165384 A1 * | 7/2005 | Gravesen et al. ........ 604/890.1 |
| 2005/0267406 A1 | 12/2005 | Hassler, Jr. |
| 2005/0267500 A1 | 12/2005 | Hassler, Jr. |
| 2005/0277974 A1 | 12/2005 | Hassler, Jr. et al. |
| 2005/0288739 A1 | 12/2005 | Hassler, Jr. et al. |
| 2005/0288740 A1 | 12/2005 | Hassler et al. |
| 2005/0288741 A1 | 12/2005 | Hassler et al. |
| 2005/0288742 A1 | 12/2005 | Giordano et al. |

FOREIGN PATENT DOCUMENTS

| | | |
|---|---|---|
| WO | WO 01/47434 | 7/2001 |

* cited by examiner

BI-DIRECTIONAL INFUSER PUMP WITH VOLUME BRAKING FOR HYDRAULICALLY CONTROLLING AN ADJUSTABLE GASTRIC BAND

CROSS REFERENCE TO RELATED APPLICATIONS

The present application is related to three co-pending and commonly-owned applications filed on even date herewith, the disclosure of each being hereby incorporated by reference in their entirety, entitled respectively:

"PIEZO ELECTRICALLY DRIVEN BELLOWS INFUSER FOR HYDRAULICALLY CONTROLLING AN ADJUSTABLE GASTRIC BAND" to William L. Hassler, Jr., Ser. No. 10/857,762;

"METAL BELLOWS POSITION FEED BACK FOR HYDRAULIC CONTROL OF AN ADJUSTABLE GASTRIC BAND" to William L. Hassler, Jr., Daniel F. Dlugos, Jr., Rocco Crivelli, Ser. No. 10/856,971;

"THERMODYNAMICALLY DRIVEN REVERSIBLE INFUSER PUMP FOR USE AS A REMOTELY CONTROLLED GASTRIC BAND" to William L. Hassler, Jr., Daniel F. Dlugos, Jr., Ser. No. 10/857,315.

FIELD OF THE INVENTION

The present invention relates, in general, to medically implantable reversible pumps, and more particularly, to such pumps that are suitable for long term use without fluid loss such as for hydraulically controlling an artificial sphincter.

BACKGROUND OF THE INVENTION

Since the early 1980s, adjustable gastric bands have provided an effective alternative to gastric bypass and other irreversible surgical weight loss treatments for the morbidly obese. The gastric band is wrapped around an upper portion of the patient's stomach, forming a stoma that restricts food passing from an upper portion to a lower portion of the stomach. When the stoma is of the appropriate size, food held in the upper portion of the stomach provides a feeling of fullness that discourages overeating. However, initial maladjustment or a change in the stomach over time may lead to a stoma of an inappropriate size, warranting an adjustment of the gastric band. Otherwise, the patient may suffer vomiting attacks and discomfort when the stoma is too small to reasonably pass food. At the other extreme, the stoma may be too large and thus fail to slow food moving from the upper portion of the stomach, defeating the purpose altogether for the gastric band.

An artificial sphincter may be utilized in any number of applications within a patient's body where it is desirable to vary the size of an orifice or organ. Depending upon the application, artificial sphincters may take the form of a flexible, substantially non-extensible band containing an expandable section that is capable of retaining fluids. The expandable section would be capable of expanding or contracting depending upon the volume of fluid contained therein. One particular example of an artificial sphincter is an adjustable gastric banding device, such as described in U.S. Pat. Nos. 4,592,339; 5,226,429; 6,102,922 and 5,449,368, the disclosure of each being hereby incorporated by reference. Adjustable gastric band implants have a hollow elastomeric balloon with fixed end points encircling a patient's stomach just inferior to the esophago-gastric junction. When saline solution is delivered into the hollow balloon, the gastric band swells and constricts the stomach, for example, for obesity reduction. Different degrees of constriction are desired, and adjustment is required over time as the patient's body adapts to the constriction.

Adding or removing saline solution from the adjustable gastric band is typically accomplished by injecting through a fluid injection port to achieve a desired diameter. Since adjustable gastric bands may remain in the patient for long periods of time, the fluid injection port is typically installed subcutaneously to reduce the likelihood of infection. Adjusting the amount of fluid in the adjustable gastric band is achieved by inserting a Huber tip needle through the skin into a silicon septum of the injection port. Once the needle is removed, the septum seals against the hole by virtue of the compressive load generated by the septum. A flexible conduit communicates between the injection port and the adjustable gastric band.

While subcutaneously implanted injection ports are a successful approach to readily adjusting a gastric band, and are a desirable feature to retain for initial installation or as a backup, it would be desirable to remotely adjust the gastric band. While minimally invasive, insertion of the Huber needle to adjust the saline solution volume does introduce increased risk of infection. In addition, this procedure typically entails the inconvenience and expense of scheduling time with a surgeon.

Some pumping methods suffer from a small amount of leakage across the pump. For example, in an implanted peristaltic pump, such as described in U.S. Pat. No. 6,102,678, a piezoelectric drive system is used to provide a rotary device that is lightweight and compact with a very small axial volume. While leakage may be of no consequence in an infuser intended to dispense fluid when the amount dispensed is measurable, the leakage may be extremely inconvenient for maintaining a constant fluid volume over an extended period of time to maintain an artificial sphincter.

Implantable infusers that contain a metal bellows accumulator are known for such uses as dispensing therapeutic drugs, such as described in U.S. Pat. No. 4,581,018. One common drawback is that implantable infusers are designed for one way controlled dispensing. Refilling the reservoir typically requires insertion of a syringe into a septum.

In an afore-mentioned co-pending application entitled "PIEZO ELECTRICALLY DRIVEN BELLOWS INFUSER FOR HYDRAULICALLY CONTROLLING AN ADJUSTABLE GASTRIC BAND" to William L. Hassler, Jr., Ser. No. 10/857,315, an advantageous infuser containing no ferromagnetic materials provides an accurately controllable volume of fluid to a closed gastric band capable of bi-directional adjustment of the fluid volume. The infuser has a titanium bellows accumulator, which may be collapsed or extended to positively displace fluid accumulated therein, thereby serving as both a reversible pump and reservoir. Thereby, a bi-directional pump that is practically immune to external magnetic fields is achieved. Such an implanted device may be used during Magnetic Resonance Imaging (MRI) without damage to the device or patient.

While this piezo-electrically driven infuser has many advantages for certain applications, it would be desirable in some applications to further reduce the size of the infuser to increase patient comfort and acceptance of the implant. In particular, it would be desirable to eliminate or greatly reduce components that surround the metal bellows accumulator while enhancing the long-term reliable performance.

Consequently, a significant need exists for a remotely controllable, bi-directional infuser that reliably locks at a selected fluid volume between adjustments.

BRIEF SUMMARY OF THE INVENTION

The invention overcomes the above-noted and other deficiencies of the prior art by providing a thermodynamically driven infuser that may be driven bi-directionally and reliably secured to maintain a selected fluid volume for the hydraulic control of implanted artificial sphincters such as gastric bands. In particular, an accumulator is expanded or collapsed by having its moving surface selectively translate along a longitudinal axis. A friction brake engaged along a braking member that is attached to the moving surface of the accumulator is selectively disengaged when adjustment is desired and then locked between adjustments. Providing a frictional brake that may be separate from an actuating mechanism for adjusting the accumulator provides benefits such as allowing a greater variety of actuating mechanisms.

In one aspect of the invention, An implantable device has an accumulator contained inside an enclosure. A portion of the accumulator is a bi-directionally movable portion that varies an internal volume of the accumulator to dispense or draw fluid. A contact surface is connected to the movable portion for bi-directional movement between a collapsed accumulator position and an expanded accumulator position. A braking member is attached to the enclosure and proximally positioned and biased into braking contact with the contact surface. When volume adjustment is desired, a brake actuator deflects the braking member away from braking contact with the contact surface, releasing the movable surface to allow pumping. Thereby, a secure, long-term volume braking capability is integral to the implantable device.

It is well recognized that medical implantable infuser pumps generally use a two-phase (liquid/gas) propellant inside a case around a metal bellows accumulator to maintain a constant pressure around the metal bellows accumulator as it changes volume. Thus, selection of a propellant with desirable pressure versus temperature characteristics around body temperature, in combination with an ability to control this propellant temperature, yields an ability to control the volume of the metal bellows accumulator, and thus a hydraulically actuated artificial sphincter. Locking the metal bellows accumulator at the desired volume then prevents inadvertent changes in volume thereafter. Thereby, a very small volume infuser is achieved.

Consequently, in another aspect of the invention, the implantable device incorporates thermal actuation of the accumulator with braking of the accumulator preventing overshoots of the desired volume and preventing susceptibility of volume changes between adjustments due to fluid pressure or temperature changes in the implantable device.

In yet another aspect of the invention, the implantable device hydraulically controls a hydraulically inflated therapeutic member. Thus, between adjustments of the hydraulically inflated therapeutic member, the braking capability of the implantable device avoids inadvertent changes in fluid volume, even if the therapeutic member is exposed to increased or described fluid pressure and other changes.

These and other objects and advantages of the present invention shall be made apparent from the accompanying drawings and the description thereof.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

DETAILED DESCRIPTION OF THE INVENTION

Implantable Hydraulically Controlled Artificial Sphincter.

Figures 1, 1A:
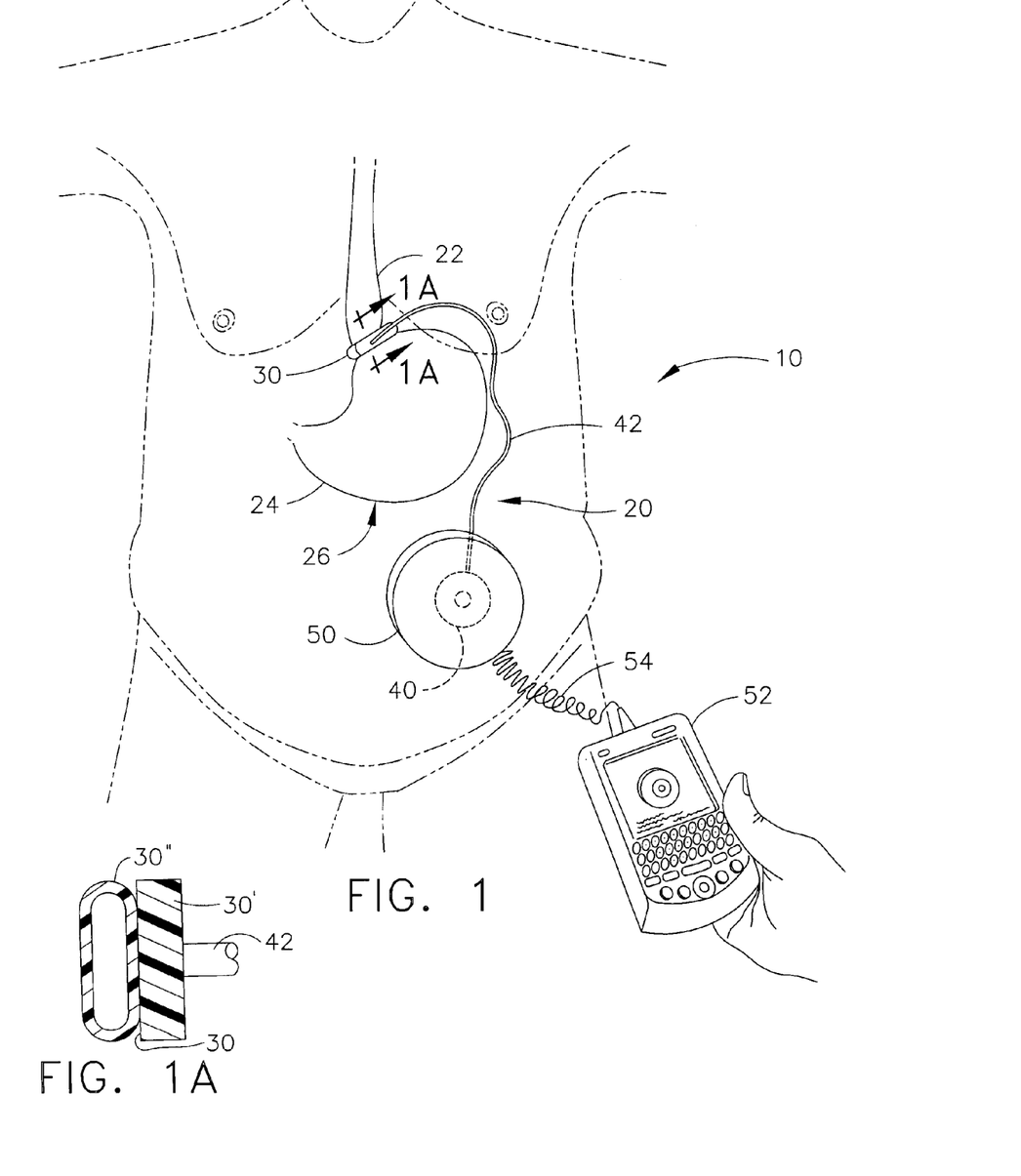
FIG. 1 is a perspective environmental view of an adjustable artificial sphincter system being remotely controlled by transcutaneous energy transfer (TET).
FIG. 1A is a cross sectional view of an adjustable gastric band taken along lines 1A-1A of the adjustable artificial sphincter system of FIG. 1.

Turning to the Drawings wherein like numerals denote like components throughout the several views, in FIG. 1, an artificial sphincter system 10 regulates the amount of fluid maintained in an implantable artificial sphincter assembly 20 used in the illustrative version for weight reduction therapy. A stoma is formed between an upper portion 22 and lower portion 24 of a patient's stomach 26 to slow the passage of food and to provide a sense of fullness. The implantable artificial sphincter assembly 20 includes an expandable gastric band 30 that encircles the stomach 26 to form the stoma. An infuser device 40 is anchored subcutaneously on a layer of muscular fascia within the patient or in another convenient location. A flexible conduit 42 provides fluid communication between the gastric band 30 and the infuser device 40.

It should be appreciated that the gastric band 30 includes an outer band 30' and an attached inwardly directed bladder 30" (FIG. 1A) to expandably receive a fluid, such as saline solution, from the infuser device 40 through the conduit 42 to allow adjustment of the size of the stoma formed therein without having to adjust the attachment of the gastric band 30. The infuser device 40 advantageously prevents fluid moving in either direction between adjustments so that long-term stability is realized.

Transcutaneous Energy Transfer (TET) and Telemetry.

An advantageous approach to further reducing the necessary size of the infuser device 40 is to utilize transcutaneous energy transfer (TET) for powering the thermodynamic actuation. Telemetry may also be utilized for functions such as commanding and/or monitoring the amount of fluid in the infuser device 40 and/or amount of fluid moved from/into the infuser device 40, especially if completing closed-loop control of the hydraulic adjustment external to the patient. The artificial sphincter system 10 may include a primary coil 50 positioned outside of the patient proximally placed to the infuser device 40 that is inside of the patient to inductively couple with a secondary coil (not shown) located within the infuser device 40. A programmer 52, which is connected via electrical cabling 54 to the primary coil 50, activates and monitors the primary coil 50.

The infuser device 40 has a rounded lozenge-shape that for clarity is described with respect to the orientation depicted in the Drawings, with what is typically outwardly oriented with respect to the skin of the patient described as upward, as the infuser device 40 would typically be oriented when placed upon a table.

The illustrative primary coil 50 has an outer diameter (OD) of about 5 inches (13 cm) and consists of one hundred and two (102) turns of litz wire made up of one hundred (100) individually insulated 30-gauge magnet wires, which are connected in parallel with 9.2 microfarads of capacitance, creating a parallel tuned resonant tank circuit with a very high Q. The secondary coil is connected in series with a capacitor to form a series tuned resonant tank circuit that is activated by receiving alternating current (AC) magnetic flux energy from the primary coil 50. The two tuned tank circuits are tuned to the same frequency for optimal power transfer.

Figure 2:
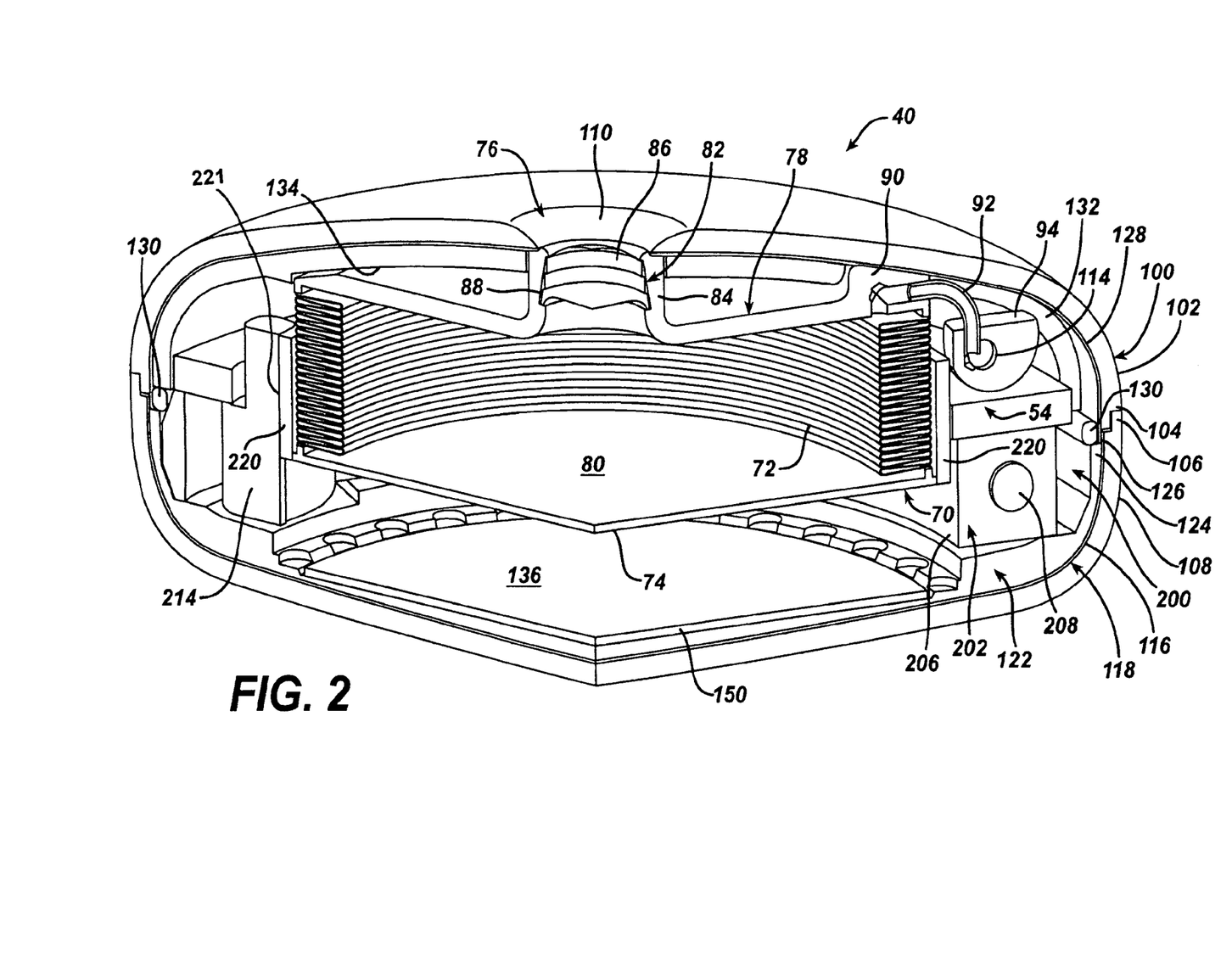
FIG. 2 is a perspective view of an implantable infuser device for bi-directional hydraulic control to an artificial sphincter band of FIG. 1, cut away to expose a thermodynamically-actuated metal bellows accumulator and piezo-electrically actuated drum brake assembly for securing the bellows accumulator.
Figure 3:
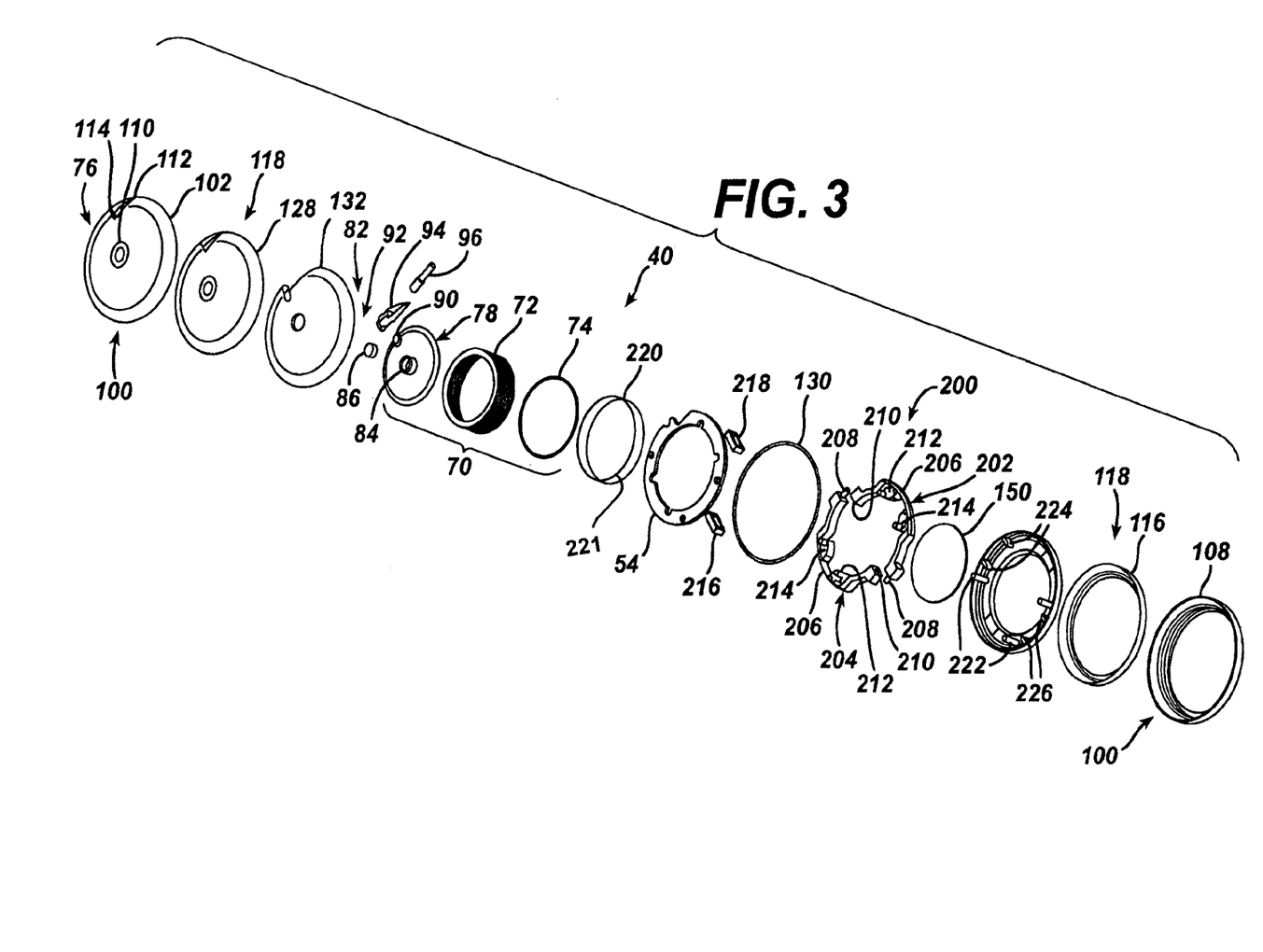
FIG. 3 is an exploded view of the implantable infuser device of FIGS. 1 and 2.
Figure 4:
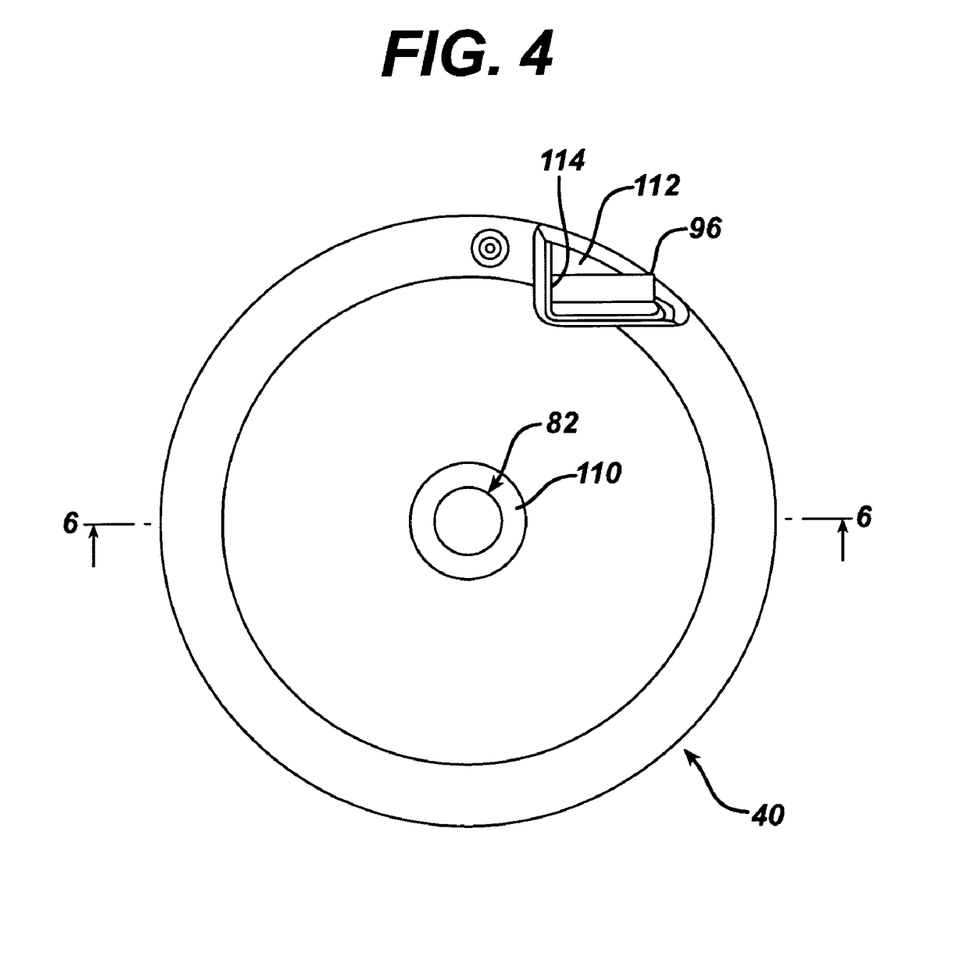
FIG. 4 is a top view of the infuser device of FIG. 1.

With particular reference to FIGS. 2-4, it should be appreciated that inductive coils (not shown) may be incorporated into infuser device 40 to receive TET power and/or for one-way or two-way telemetry communication with the external primary coil 50. Further, that position sensing (e.g., capacitive, inductive, mechanical, optical, etc) may be incorporated, such as described in the above-referenced application entitled "Metal Bellows Position Feedback for Fluid Displacement Control in a Remote Controlled Swedish Adjustable Gastric Band".

Control of such TET, telemetry, and/or position sensing within the infuser device 40 is provided by an infuser controller, depicted as a flat ring-shaped circuit board 54. In addition, the circuit board 54 is in electronic control of a thermodynamic device that either provides heating or cooling, depending on the application, as well as a braking device that selectively locks the volume of the infuser device 40 at a desired volume, with these features described in greater detail below.

Efficient power coupling of primary and secondary TET coils is described in five co-pending and co-owned patent applications filed on 24 Jun. 2004, all of which are hereby incorporated by reference in their entirety, (1)"TRANSCUTANEOUS ENERGY TRANSFER PRIMARY COIL WITH A HIGH ASPECT FERRITE CORE" to James Giordano, Daniel F. Dlugos, Jr., and William L. Hassler, Jr., Ser. No. 10/876313; (2) "MEDICAL IMPLANT HAVING CLOSED LOOP TRANSCUTANEOUS ENERGY TRANSFER (TET) POWER TRANSFER REGULATION CIRCUITRY" to William L. Hassler, Jr., Ed Bloom, Ser. No. 10/876038; (3) "SPATIALLY DECOUPLED TWIN SECONDARY COILS FOR OPTIMIZING TRANSCUTANEOUS ENERGY TRANSFER (TET) POWER TRANSFER CHARACTERISTICS" to Reshai Desai, William L. Hassler, Jr., Ser. No. 10/876057; (4) "LOW FREQUENCY TRANSCUTANEOUS TELEMETRY TO IMPLANTED MEDICAL DEVICE" to William L. Hassler, Jr., Ser. No. 10/876058; and (5) "LOW FREQUENCY TRANSCUTANEOUS ENERGY TRANSFER TO IMPLANTED MEDICAL DEVICE" to William L. Hassler, Jr., Daniel F. Dlugos, Jr., Ser. No. 10/876307.

Thermodynamically Negative Pressure Biased Metal Bellows Accumulator Infuser.

The infuser device 40 provides bi-directional hydraulic control of the gastric band 30 (not shown in FIGS. 2-3) by holding a variable amount of fluid within a bellows accumulator 70 formed from a titanium cylindrical accordion wall 72 that may be expanded and compressed along its longitudinal axis. A bellows bottom plate 74, also formed from titanium, closes off a bottom opening of the accordion wall 72 with a top opening 76 substantially sealed by a titanium bellows deck plate 78.

Fluid communication with a selectable internal volume 80 of the bellows accumulator 70 is provided by a septum 82, provided by a central spout 84 that defines the top opening 76 and is formed in the bellows deck plate 78. The septum 82 is ordinarily closed by a polymeric septum seal 86, which may be formed from a silicone material or other biocompatible material and press fit into a septum recess 88 having a circular horizontal cross section parallel to the top opening 76 in the spout 84 and a trapezoidal cross section across the longitudinal axis of the spout 84. The septum 82 allows insertion of a syringe into the selectable internal volume 80 to add or remove fluid as either a backup capability or during initial installation.

Fluid communication through the deck plate 78 of the bellows accumulator 70 is also provided by an integral access port 90 formed in the deck plate 78 that is attached to a catheter manifold tube 92, which in turn is connected to a catheter-case interface manifold 94, which in turn is connected to a catheter nipple 96 and hence to one end of the flexible conduit 42.

An outer case 100, which is formed of a biocompatible plastic, such as PEEK or polysulfone, includes a top shell 102 having a circular downwardly engaging rim 104 that mates with a circular upwardly engaging rim 106 of a bottom shell 108. The interlocking rims 104, 106 are attached to one another, such as by fusing, bonding or interference locking. The top shell 102 has a tapered centered hole 110 that guides a syringe (not shown) toward the septum 82. A tangentially directed recess 112 formed in the top shell 102 includes a catheter hole 114 (see FIGS. 2 and 4) through which the catheter nipple 96 passes and seals against.

A bottom half 116 of a thin barrier shell 118 conforms to the inside surface of the bottom shell 108 of the outer case 100 and is formed of a material such as titanium that provides a hermetic seal. Inside of the bottom half 116, a bottom carrier 122, formed of a resin or polymer, conforms to the inside surface of the bottom half 116 of the thin barrier shell 118 for locating actuating components therein and for providing thermal isolation from the outer case 100. With particular reference to FIG. 2, a rim 124 of the bottom carrier 122 is spaced slightly below the rim 106 of the bottom shell 108 and a top circumference 126 of the bottom half 116 of the thin barrier enclosure 118.

A top half 128 of the thin barrier enclosure 118 conforms to the inside surface of the titanium top shell 102 and is also formed of a material such as titanium that provides a hermetic seal and extends inside of the bottom half 116 of the thin barrier enclosure 118 with a small overlap thereto that may be welded or otherwise affixed (e.g., bonded, fused) together. A titanium-ring 130, inside of this overlapping portion of the top and bottom halves 128, 116, of the thin barrier enclosure 118, rests upon the rim 124 of the bottom carrier 122 and is compressed by a top carrier 132 that conforms to the inner surface of the top half 128 of the thin barrier shell 118. The top carrier 132 at its apex circumferentially encompasses the central spout 84 of the septum 82 and includes a downwardly defined circular recess 134 that locates the deck plate 78 of the bellows accumulator 70.

Within the outer case 100, a propellant cavity 136 is defined exterior to the bellows accumulator 70 and inside of the top and bottom carriers 132, 122 and titanium ring 130. As the bellows accumulator 70 expands, as shown in FIG. 2, the volume of the propellant cavity 136 decreases. The propellant cavity 136 contains a propellant that has both a liquid and gas phase (or saturated condition) at body temperature at approximately 37 degrees C., such as VERTREL CF that would produce a constant gauge pressure of −4 psig. Thus, rather than seeking a propellant that exerts an essentially neutral gauge pressure, a propellant that exerts a negative gauge pressure bias on the metal bellows accumulator 70 allows for thermodynamically driving a metal bellows accumulator 70 by adding heat. Thus, normal negative gauge pressure of the propellant at body temperature is harnessed for expanding the metal bellows accumulator and heating, such as by TET, is used for contracting the metal bellows accumulator 70. TET heating is achieved by inducing eddy currents that dissipate in metal components of the implant as heat. Insofar as the gastric band 30 may be under compressive pressure from adjacent body tissue, such as the stomach 26, the negative pressure bias of the propellant may be assisted by a fluid pressure in the bellows accumulator 70 as well. In some applications, such a pressure bias provides a fail-safe condition of the accumulator failing in an expanded condition, releasing pressure in an attached adjustable sphincter band.

Moving the metal bellows accumulator 70 in the opposite direction, collapsing the titanium cylindrical accordion wall 72, as depicted in FIG. 2, is achieved by adding heat to the propellant, thereby increasing pressure in the propellant cavity 136 as the propellant shifts to a gas phase from a liquid phase. This heat may be generated by various means, such as from a stored battery charge, a controlled exothermic reaction, etc. In the illustrative version, this thermodynamic heating is provided by a heat flux element, depicted as a disk-shaped thin film etched foil heater element 150, which also serves as the inductive position sensing coil and is affixed to the bottom carrier 122 opposite the bellows bottom plate 74. The thermal isolation and thermal sink provided by the outer case 100, thin barrier enclosure 118, and top and bottom carriers 132, 122 allow efficient adding of heat to the propellant without a significantly raised external temperature of the infuser device 40 that would cause discomfort or tissue damage. In some applications, more than one heat flux element of the same or different nature may be used.

Thermodynamically Positive Pressure Biased Metal Bellows Accumulator Infuser.

As an alternative to heating the propellant to thermodynamically actuate the bellows accumulator, the heat flux element 150 may comprise a thermoelectric cooler, which is a solid state heat pump based on the Peltier Effect. Thus, a propellant is selected that exerts a positive gauge pressure at body temperature, with the thermal element 150 thus used to cool the propellant to create a negative gauge pressure to expand the bellows accumulator 70. In addition or in the alternative, the thermal element 150 may be capable of both heating and cooling, such as is typical with thermoelectric coolers depending upon the direction of current flow. Thus, even greater volume reductions may be achieved in the infuser device 40 by being able to achieve a wider temperature range within the propellant, and thus a greater differential pressure range upon the bellows accumulator 70.

Piezo-Electrically Released Brake on Metal Bellows Accumulator.

Thermodynamic actuation may be harnessed in combination with various types of braking devices of the bellow accumulator 70, such as a fluid shut-off valve that prevents fluid from entering or exiting the fluid accumulator 70. In particular, it is desirable that the thermodynamic actuation occurs relatively quickly so that the clinician and patient are not inconvenienced, yet braking avoids over-shooting the desired volume. Further, the braking prevents variation in fluid volume between adjustments, such as due to compressive forces on the gastric band 30 or variations in body temperature.

Figure 5:
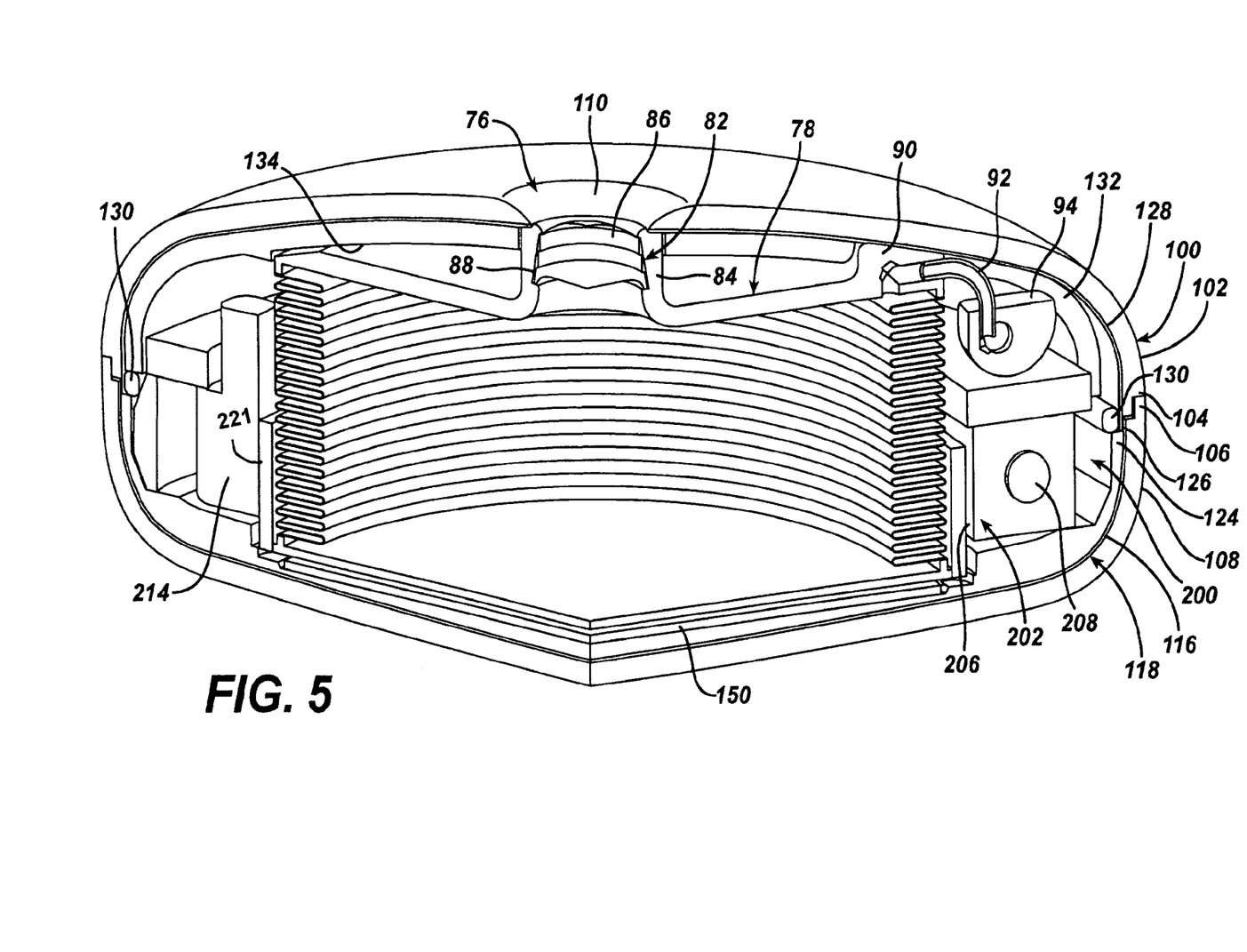
FIG. 5 is a perspective view of the implantable infuser device of FIG. 1, cut away to expose the thermodynamically actuated metal bellows accumulator in an expanded condition.
Figure 6:
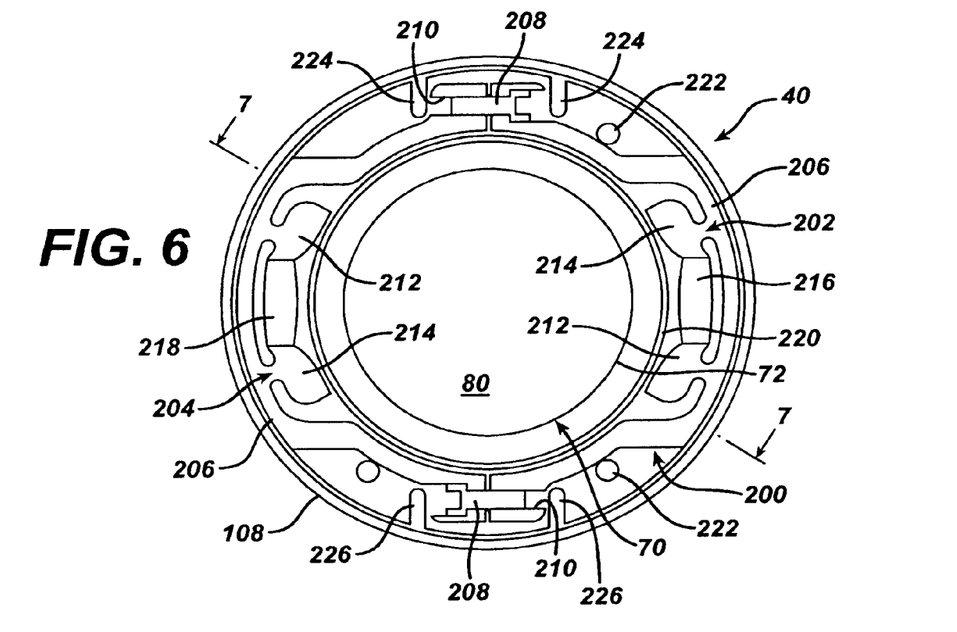
FIG. 6 is a top view in cross section along lines 6-6 of the infuser device of FIG. 4 taken through calipers and piezoelectric stack actuators of a drum brake assembly.
Figure 7:
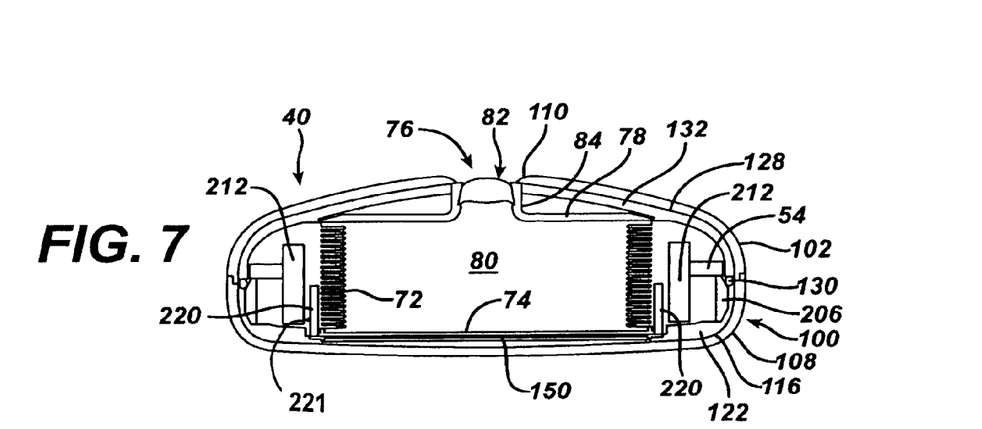
FIG. 7 is a side view in cross section taken along lines 7-7 of FIG. 6 depicting a drum brake assembly released by expanding piezo-electric stack actuators to disengage brake arms of the calipers from a brake drum attached to the metal bellows accumulator which is in an expanded condition.
Figure 8:
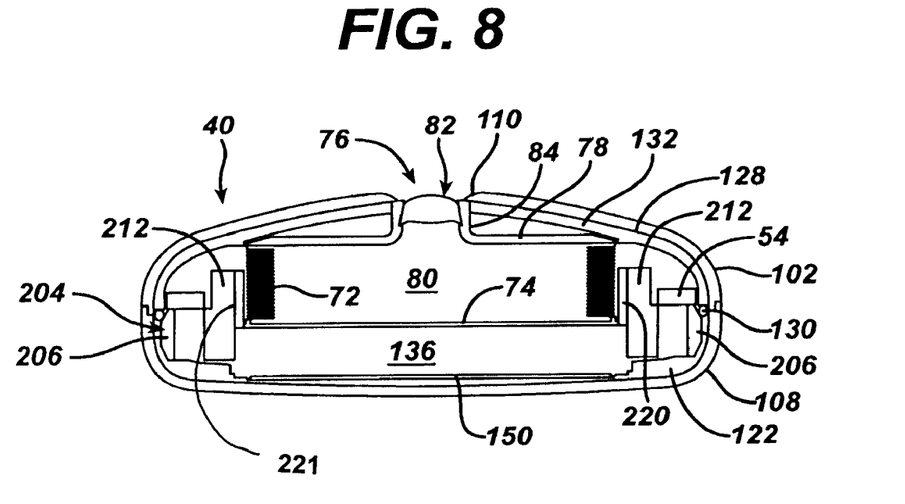
FIG. 8 is a side cross section taken along lines 7-7 of FIG. 6 depicting a drum brake assembly engaged by relaxing piezo-electric stack actuators allowing engagement of the brake arms of the calipers to the brake drum attached to the metal bellows accumulator that is in a collapsed condition.

In the illustrative version, a drum brake assembly 200, which is piezo-electrically released, provides long-term volume stability with efficient adjustment. Moreover, the piezo-electrical actuation lends itself to being practically immune from strong external electromagnetic fields, as may be advantageous for use when exposure to magnetic resonance imaging may occur. In FIGS. 2-3, 5, the components of the drum brake assembly 200 are shown to include a pair of brake calipers 202, 204, each including a semicircular band 206 with an adjustment screw 208 and screw receptacles 210 shaped to receive the adjustment screw 208 from the other caliper. A pair of rocker arms 212, 214 on each caliper 202, 204 project inwardly and are spaced apart to receive respectively a piezoelectric stack actuator 216, 218. The assembled calipers 202, 204 are set upon the bottom carrier 122 encompassing the bellows accumulator 70. In particular, a cylindrical brake drum 220 is circumferentially attached around the bellows bottom plate 74 with its longitudinal length surrounding a lower portion of the accordion wall 72. This longitudinal length is selected such that the accordion wall 72 of the bellows accumulator 70 is allowed to fully collapse before the brake drum 220 contacts the top carrier 132.

With particular reference to FIGS. 3, 6-8, the rocker arms 212, 214 are spaced away from the underlying bottom carrier 122 and the overlying circuit board 54 to allow slight horizontal deflection into and away from engagement with the brake drum 220. Specifically, stand-off posts 222, integral to the bottom carrier 122, support the circuit board 54 and the portion of the bottom carrier 122 proximal to the rocker arms 212, 214 and are slightly recessed to avoid contact. The respective screws 208 and screw receptacles 210 of the calipers 202, 204 are held in engagement with another by two pairs of partitions 224, 226 that extend upwardly from the bottom carrier 122. The longitudinal length of the brake drum 220 and the height and positioning of the rocker arms 212, 214 are selected such that the brake drum 220 presents an engaging surface 221 to the rocker arms 212, 214 through the range of volumes of the bellows accumulator 70.

In use, the gastric band 30 is strapped around the patient's stomach 26 to form a stoma that assists in the treatment of morbid obesity by inducing a sense of fullness. The flexible conduit 42 allows fluid to selectively fill an inwardly directed bladder of the gastric band 30 to adjust the stoma to a desired diameter. The infuser device 40 is attached to the other end of the flexible conduit 42 for selectively providing or withdrawing this fluid from the gastric band 30 for hydraulic control thereof. In particular, a metal bellows accumulator 70 has an initial volume that is based on the degree to which its accordion wall 72 is collapsed inside of the outer case 100. This volume is maintained by the drum brake assembly 200 that includes calipers 202, 204 that each inwardly present rocker arms 212, 214 to engage the brake drum 220. To adjust the volume, TET power and telemetry commands are communicated from the primary coil 50 to the infuser device 40. The primary coil 50 is controlled by programmer 52, with both being external to the patient. The circuit board 54 responds to received power and instructions by actuating the two piezo-electric stack actuators 216, 218, each located between a respective pair of rocker arms 212, 214. The slight growth in length spreads the pair of rocker arms 212, 214, disengaging the brake drum 220. The circuit board 54 monitors the volume of the metal bellows accumulator 70 via the position sensing coil 150 and deactivates the piezo-electric stack actuators 216, 218 when the desired volume is reached. Depending on whether the propellant is positively or negatively biasing the metal bellows accumulator 70 at body temperature and the desired direction of volume change, the circuit board 54 adjusts the temperature of the propellant in the propellant cavity 136 by activating the thermal element 150 attached to the bottom carrier 122 inside of the outer case 100. This thermal heating may be achieved through TET eddy current heating. For a negatively biased propellant, a thin film heater (e.g., inductive, resistive, Peltier effect) thus increases the pressure to collapse the bellows accumulator 70, such as going from FIG. 7 to 8, with the reverse achieved by merely releasing the drum brake assembly 200 after the propellant has cooled to body temperature. Alternatively, for a positively biased propellant at body temperature, a thermo-electric cooler (e.g., Peltier effect) is activated to expand the bellows accumulator 70, such as going from FIG. 8 to FIG. 7, with the reverse achieved by merely releasing the drum brake assembly 200 after the propellant has warmed to body temperature. Thermal isolation of the propellant and the heat flux element 150 from the patient by the heat sink and insulative properties of the infuser device avoids discomfort and tissue damage while still presenting a desirable small volume.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

For example, while versions of the infuser device described herein utilize either thermodynamically heating or cooling in combination with a particular propellant, it should be appreciated that a number of propellants may be used. Moreover, an infuser device may incorporate both heating and cooling features.

For example, it will become readily apparent to those skilled in the art that the above invention has equal applicability to other types of implantable bands. For example, bands are used for the treatment of fecal incontinence. One such band is described in U.S. Pat. No. 6,461,292, which is hereby incorporated herein by reference. Bands can also be used to treat urinary incontinence. One such band is described in U.S. Patent Application 2003/0105385, which is hereby incorporated herein by reference. Bands can also be used to treat heartburn and/or acid reflux. One such band is described in U.S. Pat. No. 6,470,892, which is hereby incorporated herein by reference. Bands can also be used to treat impotence. One such band is described in U.S. Patent Application Publ. No. 2003/0114729, which is hereby incorporated herein by reference. Further, a hydraulically inflatable therapeutic member may comprise an exteriorly adjustable bladder that actuates by expanding in length and/or outer diameter, such as a penile implant.

For another example, although use of TET has certain advantages, such as reducing the amount of components necessarily incorporated into the infuser device, applications consistent with aspects of the present invention may include infuser devices having integral power storage that does not require TET as often or at all.

As yet another example, although a cylindrical bellows accumulator is illustrated, it should be appreciated that a bellows similar to a blacksmith bellows may be housed within an outer case with the top and bottom cases pivotally attached to one another. For instance, full volume may be reached as the two plates pivoting about the vertical center of the case rotate away from each other until approaching each other again to define a nearly cylindrical volume. Volume sensing may include sensing the angular position of the two plates relative to each other.

For yet an additional example, although a bellows accumulator has desirable attributes for avoiding leakage, aspects of the present invention may incorporate other types of accumulators, such as bladders, rather than a metal bellows, within a piston-like constraint structure as described above. Thereby, an accumulator that may be more completely evacuated may be achieved. Further, the cross sectional shape of the accumulator may be circular as illustrated or other shapes such as rectangular.

As yet a further example, infusers that incorporate accumulators that include other types of pumps or electromechanical actuators to dispense or draw fluid may benefit from having a braking member consistent with aspects of the invention. Thus, the mechanical resistance inherent in the actuation mechanism need not be relied upon to prevent movement between adjustments.

What is claimed is:

1. An implantable device, comprising:
    an enclosure;
    an accumulator comprising a cylindrical bellows contained within the enclosure and including a movable portion operably configured to vary an internal volume of the accumulator in relation to linear motion of the movable portion;
    a contact surface external to the accumulator and connected to the movable portion for bi-directional movement between a collapsed accumulator position and an expanded accumulator position, the contact surface comprising a brake drum externally aligned parallel to the linear motion of the movable portion;
    a braking member within the enclosure and proximally positioned and operably configured for movement between a braking contact position locking the movable portion to a present position at any selected position along a range of positions of the movable portion and a noncontact position with the contact surface allowing unimpeded linear movement of the movable portion, wherein the braking member comprises at least one brake caliper encompassing at least a portion of a circumference of the brake drum; and a brake actuator comprising a piezo-electric stack actuator operably configured to selectively position the braking member.

2. The implantable device of claim 1, further comprising a single propellant cavity defined internal to the enclosure and external to the accumulator, the device further comprising:
a propellant having a liquid/gas phase near body temperature and present in the propellant cavity to pressure bias the accumulator for movement; and
a heat flux element operably configured to adjust a temperature of the propellant to reverse the pressure bias on the accumulator,
wherein the single propellant cavity actuates the movable portion bi-directionally.

3. The implantable device of claim 2, wherein at body temperature the propellant exerts a positive gauge pressure on the accumulator urging the movable portion toward the collapsed accumulator position, the heat flux element comprising a cooling element.

4. The implantable device of claim 2, wherein at body temperature the propellant exerts a negative gauge pressure on the accumulator urging the movable portion toward the expanded accumulator position, the heat flux element comprising a heating element.

5. An implantable device, comprising:
an enclosure;
an accumulator contained within the enclosure and including a movable portion operably configured to vary an internal volume of the accumulator;
a thermal pressure system operatively configured to vary pressure within the enclosure external to the accumulator to urge the movable portion of the accumulator to move;
a contact surface external to the accumulator and connected to the movable portion for bi-directional movement between a collapsed accumulator position and an expanded accumulator position;
a braking member within the enclosure and proximally positioned and biased into braking contact with the contact surface; and
a brake actuator operably configured to deflect the braking member from braking contact with the contact surface, wherein the brake actuator comprises a piezo-electric stack actuator.

6. The implantable device of claim 5, wherein the accumulator comprises a bellows accumulator.

7. The implantable device of claim 6, wherein the accumulator comprises a cylindrical bellows accumulator, the contact surface comprising a brake drum.

8. The implantable device of claim 7, wherein the braking member comprises at least one brake caliper encompassing at least a portion of a circumference of the brake drum.

9. The implantable device of claim 5, wherein the thermal pressure system comprises:
a single propellant cavity defined internal to the enclosure and external to the accumulator, the device further comprising:
a propellant having a liquid/gas phase near body temperature and present in the propellant cavity to pressure bias the accumulator for movement; and
a heat flux element operably configured to adjust a temperature of the propellant to reverse the pressure bias on the accumulator,
wherein the single propellant cavity actuates the accumulator bi-directionally.

10. The implantable device of claim 9, wherein at body temperature the propellant exerts a positive gauge pressure on the accumulator urging the movable portion toward the collapsed accumulator position, the heat flux element comprising a cooling element.

11. The implantable device of claim 9, wherein at body temperature the propellant exerts a negative gauge pressure on the accumulator urging the movable portion toward the expanded accumulator position, the heat flux element comprising a heating element.

12. An implanted apparatus, comprising:
a hydraulically inflatable therapeutic member; and
an infuser device in fluid communication with the hydraulically inflatable therapeutic member for adjusting a fluid volume therein, the infuser device comprising:
an enclosure;
an accumulator contained within the enclosure and including a movable portion operably configured to vary an internal volume of the accumulator;
a contact surface external to the accumulator and connected to the movable portion for bi-directional movement between a collapsed accumulator position and an expanded accumulator position;
a braking member within the enclosure and proximally positioned and biased into braking contact with the contact surface; and
a brake actuator operably configured to deflect the braking member from braking contact with the contact surface, wherein the brake actuator comprises a piezo-electric stack actuator.

13. The implanted apparatus of claim 12, wherein the hydraulically inflatable therapeutic member comprises an implantable band operably configured to encircle a bodily lumen of a patient and including an inwardly directed fluid bladder for adjusting an inner diameter.

14. The implanted apparatus of claim 13, further comprising a transcutaneous energy transfer system including a primary coil external to a patient and a secondary coil in electrical communication with the infuser device.

15. The implanted apparatus of claim 13, further comprising a thermal pressure system operatively configured to vary pressure within the enclosure external to the accumulator to urge the movable portion of the accumulator to move.

* * * * *